United States Patent [19]
Pappolla

[11] Patent Number: 5,958,964
[45] Date of Patent: Sep. 28, 1999

[54] USE OF MELATONIN TO PREVENT CYTOTOXIC EFFECTS OF AMYLOID BETA PROTEIN

[75] Inventor: Miguel A. Pappolla, Mobile, Ala.

[73] Assignee: South Alabama Medical Science Foundation, Mobile, Ala.

[21] Appl. No.: 08/801,301

[22] Filed: Feb. 18, 1997

[51] Int. Cl.$^6$ ..................................................... A01N 43/38
[52] U.S. Cl. ........................................... 514/415; 548/469
[58] Field of Search .................................. 514/415, 292; 548/469

[56] References Cited

U.S. PATENT DOCUMENTS

| | | | |
|---|---|---|---|
| 5,449,690 | 9/1995 | Lesieur et al. | 514/596 |
| 5,464,872 | 11/1995 | Langlois et al. | 514/630 |
| 5,470,846 | 11/1995 | Sandyk | 514/159 |
| 5,541,228 | 7/1996 | Takaki et al. | 514/630 |
| 5,552,418 | 9/1996 | Depreux et al. | 514/348 |
| 5,552,428 | 9/1996 | Fraschini et al. | 514/415 |
| 5,554,642 | 9/1996 | Langolis et al. | 514/415 |
| 5,580,878 | 12/1996 | D'Orlando et al. | 514/292 |
| 5,591,775 | 1/1997 | Depreux et al. | 514/580 |
| 5,596,019 | 1/1997 | Mattson et al. | 514/629 |
| 5,707,652 | 1/1998 | Lewy | 424/457 |

OTHER PUBLICATIONS

Mishima, K. et al., Acta Psychiat Scand 89:1–7 (1994).
Huerto–Delgadillo, L., et al., J Pineal Res 17:55–62 (1994).
Dori, D., et al., Chronobiol 21:121–126 (1994).
Iguchi, H., et al., J Clin Endocrinol Metabol 55:27–29 (1982).
Pappolla, M.A., et al., Mol Chem Neuropathol 28:21–34 (1996).
Pieraoli, W., Aging 3 (2):99–101 (1991).
Pierpaoli, W., et al., Ann NY Acad Sci 621:291–313 (1991).
Reiter, R.J., Exp Gerontol 30:199–212 (1995).
Skene, D.J., et al., Brain Research 528:170–174 (1990).
Souetre, E., et al., Am J Psychiatry 146:1037–1040 (1989).
Mattson, M.P., Ann NY Acad Sci 747:50–76 (1994).
Hensley, K., et al., Proc Natl Acad Sci USA 91(8):3270–3274 (1994).
Pappolla, J. Neurosci. 17, 1683, 1997.

*Primary Examiner*—Cecilia J. Tsang
*Assistant Examiner*—David Lukton
*Attorney, Agent, or Firm*—Braman & Rogalskyj, LLP

[57] ABSTRACT

The present invention is directed to a method of preventing cytotoxic effects of amyloid beta protein on cells. The method comprises exposing the cells to an effective amount of melatonin. The invention further provides a method of treating Alzheimer's disease in a human subject, which comprises administering an amount of melatonin effective to prevent the cytotoxic effects of amyloid beta protein to the human subject.

13 Claims, 3 Drawing Sheets

USE OF MELATONIN TO PREVENT CYTOTOXIC EFFECTS OF AMYLOID BETA PROTEIN

The subject matter of this application was made with support from the United States Government (National Institutes of Health Grant No. 5RO1 AG11130.

FIELD OF THE INVENTION

The present invention relates to a use of melatonin, and more particularly to the use of melatonin to prevent cytotoxic effects of amyloid beta protein.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

It is estimated that ten percent of persons older than 65 years of age have mild to severe dementia. Alzheimer's disease (AD) is the most common cause of chronic dementia with approximately two million people in the United States having the disease. Although once considered a condition of middle age, it is now known that the histopathologic lesions of Alzheimer's disease (i.e., neuritic amyloid plaques, neurofibrillary degeneration, and granulovascular neuronal degeneration) are also found in the brains of elderly people with dementia. The number of such lesions correlates with the degree of intellectual deterioration. This high prevalence, combined with the rate of growth of the elderly segment of the population, make dementia (and particularly AD) one of the most important current public health problems.

Deposition of cerebral amyloid is a primary neuropathologic marker of Alzheimer's disease. The amyloid is composed of a 40–42 amino acid peptide called the amyloid beta protein (Aβ) (Glenner and Wong, 1984). Amyloid deposits in AD are found mainly as components of senile plaques, and in the walls of cerebral and meningeal blood vessels (Robakis and Pangalos, 1994).

Molecular cloning showed that Aβ comprises a small region of a larger amyloid precursor protein (APP) (Robakis et al., 1987; Weidemann et al., 1989). Briefly, this is a type I integral membrane glycoprotein having a large extracytoplasmic portion, a smaller intracytoplasmic region, and a single transmembranous domain. APP undergoes extensive post-translational modifications (Pappolla and Robakis, 1995; Robakis and Pangalos, 1994) prior to the secretion of its N-terminal portion (Sambamurti et al., 1992; Robakis and Pangalos, 1994). Physiologic processing of APP involves cleavage within the Aβ sequence by an unidentified enzyme, alpha-secretase (Anderson et al., 1991). Smaller quantities of APP molecules are cleaved at two other sites that could potentially produce amyloidogenic secreted or membrane bound APP (Robakis and Pangalos, 1994). Aβ is also produced during normal cellular metabolism (Haass et al., 1992; Shoji et al., 1992).

There is some controversy as to whether amyloid causes AD; however, three main lines of evidence have strengthened the amyloid hypothesis. The first piece of evidence is provided by the identification of several point mutations within the APP gene. These mutations segregate within a subgroup of patients afflicted with a familial form of the disorder and thus suggest a pathogenetic relationship between the APP gene and AD (Chartier-Harlin et al., 1991; Kennedy et al., 1993). Secondly, amyloid deposition temporally precedes the development of neurofibrillary changes (Pappolla and Robakis, 1996) and this observation is also consistent with a link between amyloid and neuronal degeneration. Finally, it has been shown that Aβ is toxic to neurons (Yankner et al., 1990; Behl et al., 1992; Behl et al., 1994; Zhang et al., 1994), a finding that also strengthened the hypothesis that the amyloid peptide may contribute to the neuronal pathology in AD.

The finding that Aβ has neurotoxic properties has provided a possible connection between amyloid accumulation and neurodegeneration. After a number of controversial reports, studies from several laboratories have now corroborated this observation and demonstrated that the effects of the peptide are dependent on aggregation (Busciglio et al., 1992; Pike et al., 1993), time of exposure, osmolarity, pH and concentration (Burdick et al., 1992; Pik et al., 1993). The mechanism of toxicity is not totally understood. In addition to free-radicals, increased sensitivity to excitotoxicity (Copani et al., 1995) and/or disruption of $Ca^{2+}$ homeostasis (Mattson et al., 1992; Mattson et al., 1993; Le et al., 1995; Mark et al., 1995) seem to be involved. The magnitude of the damage contributed by each of these factors and the extent of their interaction are unresolved issues (Busciglio et al., 1993; Mattson, 1994; Weiss et al., 1994; Copani et al., 1995). Because of the close association between aging and AD and the similarities in the neuropathology of both conditions, oxidative stress has been proposed to play a role in the pathogenesis of AD lesions.

Several investigators demonstrated that oxygen free-radicals (OFRs) are related to the cytotoxic properties of Aβ (Behl, 1992; Behl, 1994; Harris et al., 1995; Butterfield et al., 1994; Goodman and Mattson, 1994). Such findings are important, since markers of oxidative injury are topographically associated with the neuropathologic lesions of AD (Pappolla et al., 1992; Furuta et al., 1995; Smith et al., 1995; Pappolla et al., 1996). Because of these observations, antioxidants have been proposed as potential therapeutic agents in AD (Mattson, 1994; Hensley et al., 1994; Pappolla et al., 1996).

Interestingly, melatonin exhibits antioxidant properties (Reiter, 1995), but, in contrast to conventional antioxidants, this hormone has a proposed physiologic role in the aging process (Pierpaoli, 1991; Pierpaoli et al., 1991) and decreased secretion of melatonin with aging is documented (Iguchi et al., 1982; Dori et al., 1994). There are reports of more profound reductions of melatonin secretion in populations with dementia than in non-demented controls (Souetre et al., 1989; Mishima et al., 1994). It has been suggested that altered secretion levels of the hormone may partially reflect the loss of daily variation in the concentration of melatonin in the pineals of elderly individuals and AD patients (Skene et al., 1990). These facts regarding melatonin are in sharp contrast with conventional antioxidants which despite their reported cytoprotective characteristics have no comparable correlates with the pathophysiology of human aging.

The effects of melatonin are complex. In addition to its OFR scavenging properties, melatonin interacts with calmodulin (Benitez-King and Anton-Tay, 1993), microtubular components (Benitez-King and Anton-Tay, 1993), and is reported to increase the activity of the intrinsic cellular antioxidant defenses (Huerto-Delgadillo et al., 1994).

A need continues to exist for methods of treating AD.

SUMMARY OF INVENTION

To this end, the subject invention provides a method of preventing cytotoxic effects of amyloid beta protein on cells.

The method comprises exposing the cells to an effective amount of melatonin. The invention further provides a method of treating Alzheimer's disease in a human subject, which comprises administering an amount of melatonin effective to prevent the cytotoxic effects of amyloid beta protein to the human subject.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION

The subject invention provides a method of preventing cytotoxic effects of amyloid beta protein on cells. The method comprises exposing the cells to an effective amount of melatonin.

As used herein, "amyloid beta protein" (Aβ) refers to the 40–42 amino acid peptide that makes up the cerebral amyloid which is the primary neuropathologic marker of Alzheimer's disease (AD), and refers to fragments of the Aβ capable of causing cytotoxic effects on cells. For example, one such fragment of Aβ is the fragment made of up amino acid residues 25–35 of Aβ (see Glenner and Wong 1984 for the full amino acid sequence of Aβ, which is hereby incorporated by reference).

As further used herein, "melatonin" refers to the compound N-[2-(5-Methoxyindol-3-yl)ethyl]acetamide (also referred to as N-acetyl-5-methoxytryptamine), as well as to analogs thereof which retain the function of preventing the cytotoxic effects of Aβ. Such analogs, as used herein, include compounds that interact with melatonergic systems, for example, compounds that interact with the melatonin receptor. Many examples of such compounds are known in the art. See, for example, U.S. Pat. Nos. 5,449,690, 5,464,872, 5,470,846, 5,541,228, 5,552,418, 5,552,428, 5,554,642, 5,580,878, and 5,591,775, the contents of each of which are hereby incorporated by reference. Analogs can readily be assayed to ensure that the function of preventing the cytotoxic effects of Aβ is retained using the methodology disclosed herein, such as assays for cell viability, lipid peroxidation, intracellular $Ca^{2+}$, and oxygen free-radicals. The prevention of other cytotoxic effects of Aβ on cells can readily be observed microscopically, such as the prevention of membrane blebbing, cell retraction, abnormal distribution of chromatin, and karyorrhexis.

As indicated above, the cytotoxic or cell killing effects of Aβ include, for example, decreased cell viability (i.e. cell death), increased lipid peroxidation (an indicator of increased oxygen free-radicals), increased intracellular $Ca^{2+}$, levels, diffuse membrane blebbing, cell retraction, abnormal distribution of chromatin towards the nuclear membrane, and karyorrhexis.

The cytotoxic effects of Aβ are most readily seen in neuronal cells (including cells of the central and peripheral nervous systems), and occur in human subjects afflicted with Alzheimer's disease.

Figure 5:
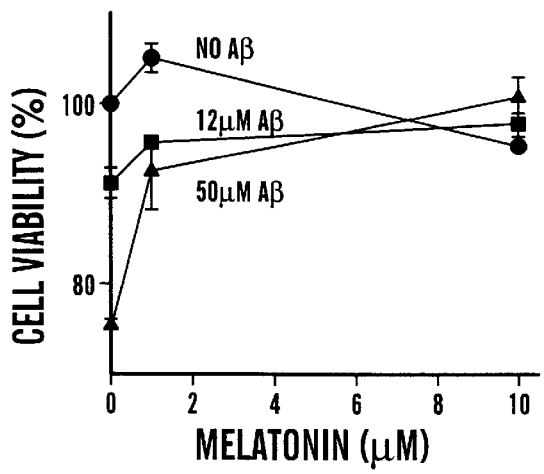
FIG. 5 shows the effect of melatonin on the viability of N2a cells exposed to Aβ(25–35)

The effective amount of melatonin for prevention of the cytotoxic effects can also be readily determined. As discussed in the examples which follow, about 1 to about 100 $\mu$M of melatonin is effective to prevent the cytotoxic effects of 50 $\mu$M Aβ(25–35) and of 100 $\mu$M Aβ(1–40) in vitro, with 5 and 10 $\mu$M of melatonin being presently preferred. FIG. 5 shows dose responses for varying Aβ(25–35) and melatonin concentrations.

For in vivo prevention of cytotoxic effects, the presently preferred dosage is between about 1 $\mu$g and about 100 g of melatonin. Desirable serum concentrations of melatonin are in the range of about 50 $\mu$M to about 100 $\mu$M. It will be appreciated that the actual preferred amount of melatonin to be administered according to the present invention will vary according to the particular form of melatonin (for example, melatonin or an analog thereof), the particular composition formulated, and the mode of administration. Many factors that may modify the action of the melatonin can be taken into account by those skilled in the art; e.g., body weight, sex, diet, time of administration, route of administration, rate of excretion, condition of the subject, drug combinations, and reaction sensitivities and severities. Administration can be carried out continuously or periodically within the maximum tolerated dose. Optimal administration rates for a given set of conditions can be ascertained by those skilled in the art using conventional dosage administration tests.

The invention further provides a method of treating Alzheimer's disease in a human subject which comprises administering an amount of melatonin effective to prevent the cytotoxic effects of Aβ to the human subject. The dosage amount is discussed above, and suitable routes of administration include systemic administration (because the melatonin will cross the blood-brain barrier). Systemic administration includes parenteral and oral administration, for example, as discussed in further detail below.

The melatonin (including melatonin and analogs thereof) may be administered alone or in combination with compatible carriers as a composition. Compatible carriers include suitable pharmaceutical carriers or diluents. The diluent or carrier ingredients should be selected so that they do not diminish the therapeutic effects of the melatonin as used in the present invention.

The compositions may be made up in any suitable form appropriate for the desired use; e.g., oral, parenteral, or topical administration. Suitable dosage forms for oral use include tablets, dispersible powders, granules, capsules, suspensions, syrups, elixirs, and skin patches. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

Therapeutic strategies could also involve gene regulation strategies, including gene therapy, to increase secretion of melatonin by modulating its synthetic pathway.

Having thus described the subject invention, the following examples demonstrate that melatonin, a pineal hormone with recently established antioxidant properties, is remarkably effective in preventing death of cultured neuroblastoma cells as well as oxidative damage and intracellular $Ca^{2+}$ increases induced by a cytotoxic fragment of A$\beta$. The effects of melatonin are extremely reproducible and are corroborated by multiple quantitative methods (including cell viability studies by confocal laser microscopy, electron microscopy, and measurements of intracellular calcium levels).

Materials and Methods
Cell viability studies

Most experiments were performed with murine N2a neuroblastoma cells using A$\beta$(25–35), although a number of confirming experiments were performed using PC12 cells and A$\beta$(1–40) (see below). N2a cells were chosen for most of the experiments because these cells exhibit larger cytoplasmic areas and better attachment to plates than PC12 cells, allowing better morphologic analysis of cell damage. N2a cells were exposed to various concentrations of A$\beta$(25–35), the actively toxic fragment of A$\beta$ (Yankner et al., 1990), or to matching concentrations of a control scrambled sequence SEQ ID NO:1: KSGNMLGIIAG for various time periods. A$\beta$(25–35) and the scrambled peptide were obtained from Research Genetics (Huntsville, Ala.) using identical methods of synthesis for both sequences. Melatonin and A$\beta$(1–40) were purchased from Sigma Co. (St. Louis, Mo.). Cells were grown in serum-free Dulbecco's modified Eagle medium supplemented with 5 $\mu$g/ml insulin, 20 $\mu$M progesterone, 100 $\mu$g/ml transferrin, 40 $\mu$M selenium and 100 $\mu$M putrescine. To insure the reliability and reproducibility of the observations, the cytotoxic effects of A$\beta$(25–35) on N2a cells and the actions of melatonin were assessed by several methodologies. These included fluorescent staining with the probe Bodipy Green (Molecular Probes, Eugene, Oreg.) which is a reliable indicator of viability (Poot et al., 1991), dual fluorescent labelling using annexin V-FITC and propidium iodide (R & D Systems, Minneapolis, Minn.) (Koopman et al., 1994; Vermes et al., 1995), scanning and transmission electron microscopy (Hayat, 1986), and the trypan blue exclusion method (Pike et al., 1993). The rationale to use annexin in the measurements is as follows: During apoptosis cells expose phosphatidylserine of the outer membrane which dramatically increases binding of annexin V (red fluorescence). Cells undergoing apoptosis characteristically bind annexin V and exclude propidium iodide (Koopman et al., 1994; Vermes et al., 1995). In contrast, staining with both propidium iodide and annexin V has been associated with necrosis (Koopman et al., 1994; Vermes et al., 1995). Although apoptosis is defined by more than one single feature, this method is used as one additional indicator of the phenomenon reported here. Labelling studies with Bodipy Green, annexin and propidium iodide were analyzed by scanning laser confocal microscopy (Koopman et al., 1994; Vermes et al., 1995) using a Molecular Dynamics (Sunnyvale, Calif.) scanning microscope. Ultrastructural examination was performed because it allowed direct visualization of cell damage including induction of membrane blebs by A$\beta$ and cell retraction, as well as abnormalities in chromatin distribution and karyorrhexis. Cells exhibiting increased membrane blebs and/or shrinking (retraction) were counted at low magnifications and compared with control preparations exposed to the scrambled peptide or melatonin alone. Details on concentrations of A$\beta$(25–35), melatonin and/or scrambled peptide (control) and incubation times used in the experiments are indicated.

At a minimum, all reported experiments, except where indicated, were performed in duplicate and reproduced in different days. However, to further ensure reproducibility of the findings, the trypan blue method was used to measure the viability of PC12 cells exposed to A$\beta$(25–35) and of N2a and PC12 cells exposed to A$\beta$(1–40). PC12 cells were handled in a manner identical as described for N2a cells except that they were grown on collagen coated plates. Additional control experiments included treatment with the spin trap n-tert-butyl-$\alpha$-phenyl nitrone (PBN) instead of melatonin, as well as adriamycin (see corresponding figures). PBN is an OFR scavenger chemically unrelated to melatonin and since it has previously been used in studies involving A$\beta$ toxicity (Behl, 1994), it was used here to verify the reliability of the viability measurements. Adriamycin has been used in several studies as a cell killing agent (Marin et al., 1996) and it was included as an additional control in some experiments.

Intracellular $Ca^{2+}$ studies

The fluorescent probe Fluo-3 was used for measurements of $Ca^{2+}$ as described (Minta et al., 1985). Control cells (with or without addition of scrambled peptide) and cells exposed to A$\beta$ or A$\beta$ with melatonin were incubated with 2 $\mu$M Fluo-3 for 15 minutes (see figures). The cells were scanned for maximum fluorescence by scanning laser confocal microscopy using a section series. The images with the highest fluorescence were subjected to 3D FishNet modeling to obtain relative fluorescence intensity (RFI) measurements and section line "cutting" for histogram determination of $Ca^{2+}$ levels using the Silicon Graphics software. Calibration for quantitative measurements of $Ca^{2+}$ was achieved with a commercially available kit (Molecular Probes, Eugene, Oreg.).

Lipid peroxidation

To verify that melatonin is a free radical scavenger in the system under study, the degree of lipid peroxidation was measured in parallel experiments in which N2a cells were either exposed to A$\beta$(25–35), or the superoxide dismutase (SOD) inhibitor diethyldithiocarbamic acid (DDTC) (positive control) with or without melatonin. Under these experimental conditions, the degree of lipid peroxidation was estimated by measuring the formation of malondialdehyde acid (MDA) in cell lysates as described (Omar et al., 1987).

EXAMPLE I

Melatonin prevents death of neuroblastoma cells exposed to Aβ

Figure 1:
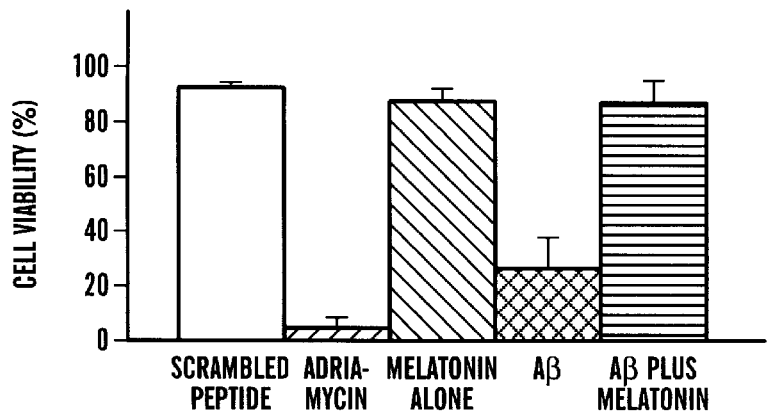
FIG. 1 shows the effect of melatonin on the viability of cells exposed to Aβ(25–35)

Addition of melatonin to culture plates exposed to Aβ(25–35) showed a striking improvement in cell survival. FIG. 1 shows cell viability counts as assessed with the fluorescent Bodipy Green probe. N2a cells were plated and after 24 hours, during exponential growth phase, treated with either scrambled peptide (control), adriamycin (control for apoptotic cell death (Marin et al., 1996)), 50 μM Aβ(25–35), or 50 μM Aβ(25–35) with 10 μM melatonin for 24 hr. Live cells were assessed by their fluorescence with Bodipy Green. Results are reported as means ± standard deviation of 4 experiments (2 duplicate experiments on different days, minimum 100 cells studied per plate). * indicates measurements significantly different from control (p<0.02, paired t-test). Images were also obtained with Bodipy Green and with dual fluorescent labeling with annexin V (red)/propidium iodide (green). Cultured N2a cells were exposed for 24 hr to either scrambled peptide; 50 μM Aβ(25–35); or 50 μM Aβ(25–35) plus 10 μM melatonin. Following exposure to Aβ(25–35) alone many cells showed a marked decrease in fluorescent intensity with Bodipy Green, reflecting decreased cell viability. Images were also obtained from cells exposed to Aβ(25–35) and then stained by a dual fluorescent tagging method with the probes annexin V-FITC (red) and propidium iodide (green). Following examination with the appropriate filters, the number of cells that stained simultaneously with both markers (necrosis) or with annexin V only (apoptosis) were counted. Exposure of cells to 50 μM Aβ(25–35) was followed by an almost exclusive increase in the number of cells exhibiting red fluorescence only (annexin V). By 24 hr, 70±25% of the cells exposed to Aβ(25–35) developed strong red (annexin) fluorescence and no increase in propidium iodide (green) fluorescence (means ± standard deviation represent 2 duplicate different day experiments, 4 experiments total; minimum 300 cells/plate counted). Such effects were prevented by simultaneous addition of melatonin to the culture medium (at 24 hr, 20 +/− 10% annexin positive cells were counted in plates containing Aβ (25–35) plus melatonin and 15 +/− 10% annexin positive cells in control plates containing scrambled peptide alone).

Figure 2:
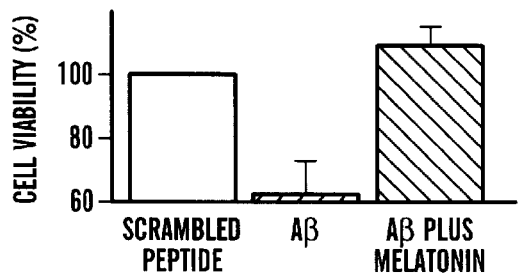
FIG. 2 shows the effect of melatonin on the viability of PC12 cells exposed to Aβ(25–35)
Figure 3:
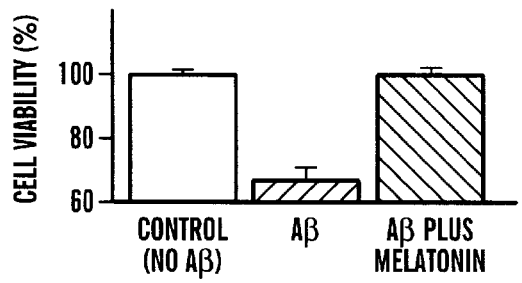
FIG. 3 shows the effect of melatonin on the viability of N2a cells exposed to Aβ(1–40)

Exposure of cells to Aβ(25–35) induced cell death in over two thirds of the cells by 24 hr (as assessed by the above mentioned methods), while simultaneous addition of melatonin to the culture medium prevented cell death. Decreased cell viability with Bodipy Green was determined by counting the number of cells exhibiting decreased fluorescent intensity. With the annexin/propidium iodide method, the number of cells showing simultaneous fluorescence staining with annexin V and propidium iodide in the same cells were counted (necrosis) as well as the number of cells staining with annexin V only (apoptosis). Under the experimental conditions used, an almost exclusive increase in red fluorescent cells after exposure to Aβ(25–35) was found. This increase was prevented by the addition of melatonin. The number of cells exhibiting increased fluorescence with propidium iodide after exposure to Aβ alone was comparable to control plates incubated with scrambled peptide, suggesting that apoptosis is the mode of cell death at the indicated concentration of Aβ(25–35) in N2a cells. Cell survival appeared dependent on concentration of Aβ(25–35) and time of exposure, as previously noted by several laboratories. By electron microscopy, the effect of Aβ(25–35) as well as the described phenomenon with melatonin were readily apparent. Exposure of cells to Aβ(25–35) resulted in marked cell damage characterized by diffuse membrane blebbing (defined as the percentage of cells exhibiting diffuse involvement by large and small blebs on more than one half of their surface), cell retraction, abnormal distribution of chromatin towards the nuclear membrane, and karyorrhexis (defined as fragmentation and condensation of nuclear material into large electron dense granules). Quantitation of cell retraction and/or increased membrane blebs showed that these toxic effects were prevented by melatonin. Table 1 shows quantitative differences observed between control cells (scrambled peptide) and cells incubated with Aβ(25–35) or Aβ(25–35) plus melatonin. Cultured N2a cells were exposed to 50 μM Aβ(25–35) or to scrambled peptide (controls) for 12 hr. The number of cells exhibiting conspicuous numbers of large blebs (more than half of the cell surface involved) or retraction of their soma were counted (see FIGS. 2 and 3) and compared to cultures exposed to Aβ plus melatonin. While both groups treated with Aβ were significantly different (p<0.005) from the control (scrambled) the group treated with melatonin was also significantly different (p<0.005) from the group treated with Aβ alone.

Figure 4:
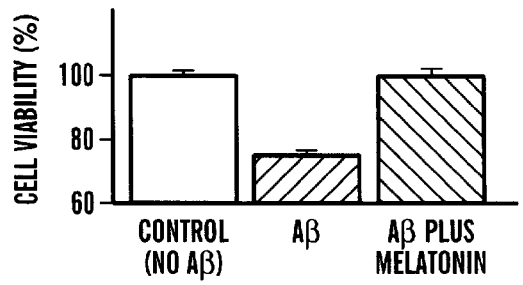
FIG. 4 shows the effect of melatonin on the viability of PC12 cells exposed to Aβ(1–40)

Results of the experiments on PC12 cells exposed to Aβ(25–35) (assessed by the trypan blue method) (FIG. 2) and on N2a and PC12 cells exposed to Aβ(1–40) (FIGS. 3 and 4, respectively) corroborated the reproducibility of the findings beyond a particular cell line and with the more physiologically relevant peptide Aβ(1–40). In these experiments cells were plated as described in the previous experiments except that PC12 cells required 4 days of growth on collagen coated plates. Cells were exposed to 50 μM Aβ(25–35) (FIG. 2) or 100 μM Aβ(1–40) (FIGS. 3 and 4) for 24 hours. Melatonin, where indicated, was at 50 μM. Values represent the means ± standard deviation of 4 experiments; a minimum of 500 cells were counted per culture plate. Cell viability was assessed by trypan blue exclusion and expressed as a percentage of controls. These experiments showed that melatonin prevented cell death following exposure to the above mentioned peptides in either N2a or PC12 cells. Results were equally striking irrespective of the cell line or peptide used. The viability of cells exposed to Aβ plus melatonin was identical to control cultures.

Figure 6:
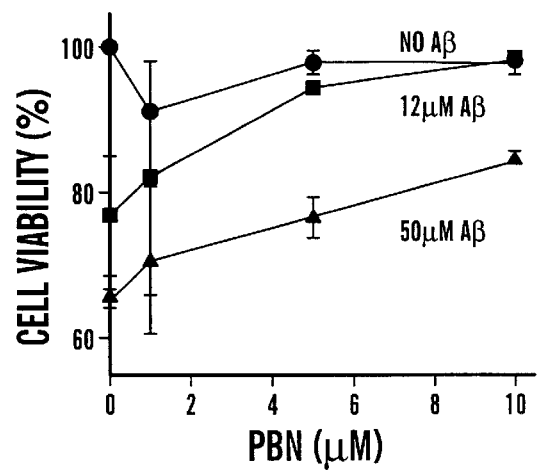
FIG. 6 shows the effect of PBN on the viability of N2a cells exposed to Aβ(25–35)

A "checkerboard" dose response experiment was also performed on N2a cells in which the effect of each of two concentrations of Aβ(25–35) were tested in permutation with either two concentrations of melatonin or without the hormone. As a control, another parallel "checkerboard" experiment was run, but instead of melatonin, PBN was used (because PBN was previously reported to enhance the survival of cells exposed to Aβ). Referring to FIGS. 5 and 6, N2a cells were plated and after 24 hr, during exponential dividing phase, exposed to the indicated concentrations of Aβ(25–35) for 6 hr and treated with either melatonin or PBN at the indicated concentrations. These experiments were performed at 6 hr because cell death was readily apparent by this time. Viable cells are expressed as a percentage of controls and assessed by their ability to exclude trypan blue. Similar dose responses were obtained by body green fluorescence. Values represent the means ± standard deviations for duplicate experiments; a minimum of 500 cells were counted per culture plate. Differences in survival between cells exposed to Aβ alone vs Aβ with melatonin were statistically significant for all concentrations of Aβ and melatonin (i.e.: 50 μM Aβ vs 50 μM Aβ+1.2 μM melatonin= p<0.002; 50 μM Aβ vs 50 μM Aβ+10 μM melatonin=p= <0.001). The results of these experiments confirmed once again the cytoprotective effects of melatonin and showed a correlation between cell survival and concentrations of Aβ and melatonin (FIGS. 5 and 6), as evaluated by the trypan blue method.

In summary, the reported effects of melatonin on preventing cell death were verified by different experimental approaches and found to be extremely reproducible and statistically significant with all the methods employed.

EXAMPLE II

Figure 7:
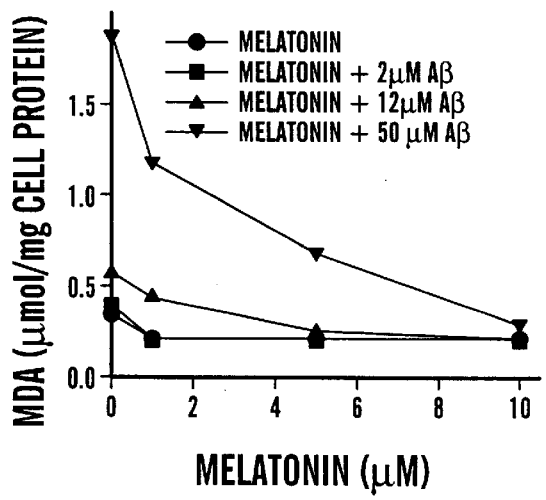
FIG. 7 shows the effect of melatonin on lipid peroxidation by cells exposed to Aβ(25–35)
Figure 8:
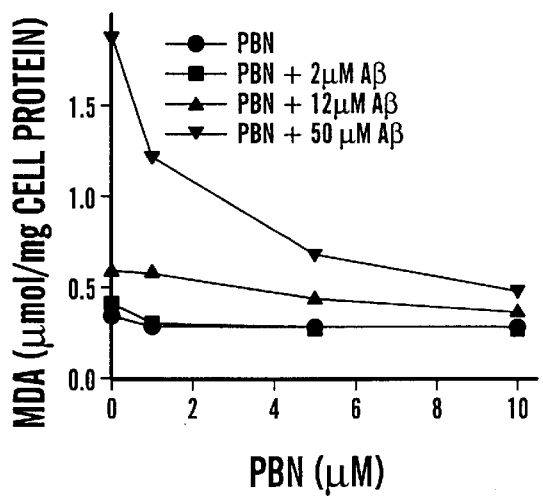
FIG. 8 shows the effect of PBN on lipid peroxidation by cells exposed to Aβ(25–35)

Melatonin and PBN prevent lipid peroxidation of cultured N2a cells induced by Aβ or inhibition of superoxide dismutase Referring to FIGS. 7 and 8, the by product malondialdehyde acid (MDA) was measured in N2a cell lysates as described (Omar et al., 1987), at the indicated concentrations of melatonin (FIG. 7), PBN (FIG. 8) and Aβ(25–35). Values are the means of three separate determinations. Standard error in all measurements was <20% of the mean. Cells were cultured and after 24 hr they were exposed to Aβ(25–35) for 24 hr with and without melatonin or PBN.

Figure 9:
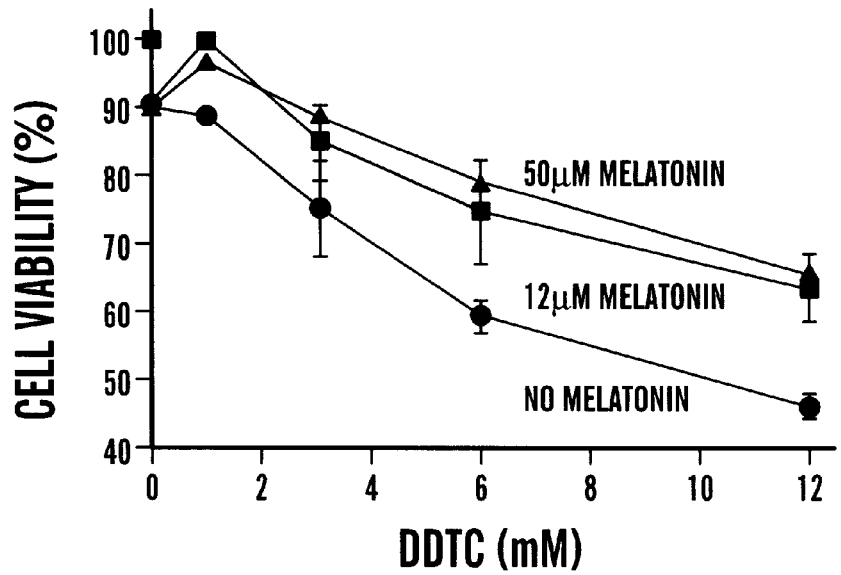
FIG. 9 shows the effect of melatonin on the viability of cells exposed to DDTC.

Referring to FIG. 9, cells were plated as previously noted in FIG. 1 and exposed to DDTC for 24 hr at the indicated concentrations. Melatonin was added at the stated concentrations. Survival was determined by the trypan blue exclusion method and expressed as percentage of controls (no DDTC). Data represents the means ± standard deviation for 4 experiments (2 duplicatd different day experiments).

Exposure of N2a cells to Aβ(25–35) or DDTC resulted in increased lipid peroxidation (FIGS. 7 and 8) and this effect was prevented by melatonin. As noted with Aβ(25–35), control experiments with DDTC also caused cell death in a concentration dependent manner (FIG. 9). These effects were prevented by addition of melatonin to the culture medium (FIGS. 7–9). The experiments with DDTC were designed to provide additional control variables as well as preliminary evidence that melatonin exhibits antioxidant activity in the system. PBN, a chemically unrelated free-radical scavenger, was also included as an additional control in the experiments for similar reasons as discussed on the section on cell survival. This substance was effective in preventing lipid peroxidation induced by Aβ(25–35) (FIG. 8) and DDTC. The cytoprotective effects of melatonin and PBN were concentration dependent (FIGS. 7–9).

EXAMPLE III

Melatonin prevents Aβ-induced intracellular $Ca^{2+}$ increase

Figure 10:
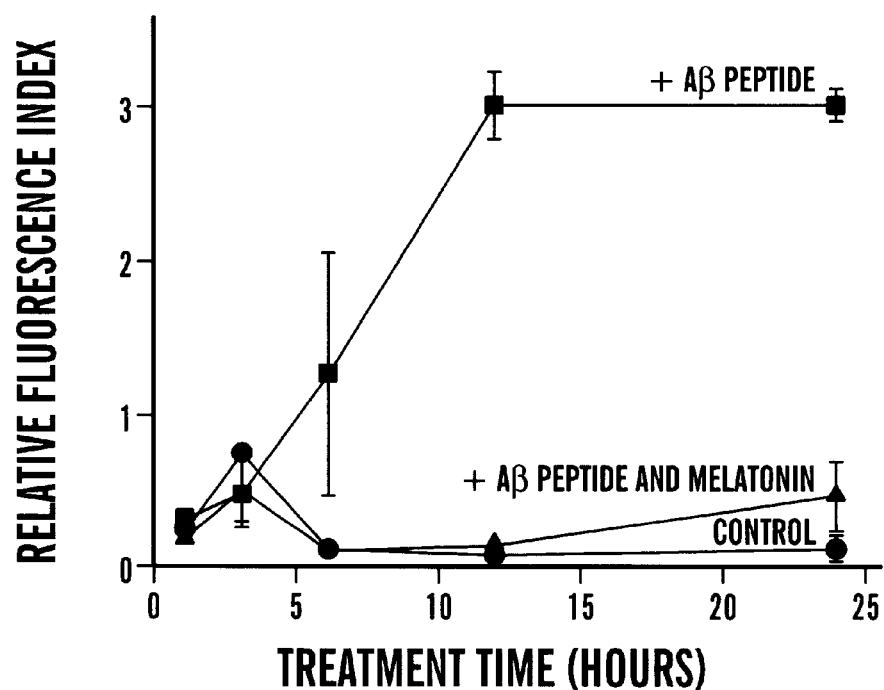
FIG. 10 shows the effect of melatonin on the relative fluorescence index of cells exposed to Aβ(25–35).

Referring to FIG. 10, cells were exposed to 50 μM scrambled peptide, 50 μM Aβ(25–35), or 50 μM Aβ(25–35) plus 5 μM melatonin. Aβ alone was significantly different than control and Aβ+melatonin after 6 hr at all time points (p<0.002). Data are expressed as means ± standard deviation of 4 experiments. There were no significant differences between control and Aβ+melatonin at any time point.

Control cells exhibited an average intracellular $Ca^{2+}$/Fluo-3 fluorescence of 0.3±0.1 RFI units (n=20 cells), while cells exposed to Aβ(25–35) showed a marked increase in intracellular $Ca^{2+}$ (Fig. 10) (at 12 hr: RFI values 0.3±0.09 and 2.2±0.2 control versus Aβ respectively; n=12 cells per plate). Inclusion of melatonin in the cultures, returned the intracellular $Ca^{2+}$ levels to near normal (RFI value, 0.55±0.2). Since adriamycin treatment has been used as a model for intracellular $Ca^{2+}$ increases during apoptosis (Marin et al., 1996), cells treated with 0.03 μg/ml adriamycin were included as a control system for the $Ca^{2+}$ studies.

EXAMPLE IV

Several methods were used to confirm that melatonin prevents death of cultured cells exposed to toxic fragments of Aβ. These methods included conventional light microscopy (trypan blue exclusion method), confocal laser microscopy using various probes for the assessment of cell viability (Bodipy Green, annexin V and propidium iodide), scanning and transmission electron microscopy, fluorescent $Ca^{2+}$ imaging, and measurements of lipid peroxidation. The bioavailability of melatonin makes it an ideal candidate for use in therapy. In vivo studies have shown that melatonin rapidly crosses the blood brain barrier following systemic administration and reaches every neuronal compartment (Menendez-Pelaez et al., 1993).

Initial in vitro evidence suggests that the cytoprotective effects of melatonin are related to its antioxidant properties. In line with such an interpretation, melatonin prevented cell death induced by inhibition of superoxide dismutase as well as Aβ-induced lipid peroxidation. Inhibition of SOD by DDTC is a well established model of oxidative injury (Omar and Pappolla, 1993) that has previously been used to induce death of spinal cord neurons via an apoptotic pathway (Rothstein et al., 1994). These observations are also in agreement with the oxidative stress hypothesis of AD.

Melatonin also blocked Aβ-related increases in intracellular $Ca^{2+}$ levels. Sulphydryl groups in membrane $Ca^{2+}$ pumps are characteristic targets of oxidative injury (Rohn et al., 1993) and damage to these structures by Aβ has been documented (Mark et al., 1995). It has been proposed that $Ca^{2+}$ plays an important role in Aβ mediated cell death (Mattson, 1994). Efflux of the ion into abnormal cellular compartments (Nicotera et al., 1992) causes activation of a number of $Ca^{2+}$ dependent degradative processes detrimental to the cell.

In AD, the magnitude of the mental impairment correlates better with the severity of neuronal damage rather than with the degree of amyloid accumulation (Hyman et al., 1985). Therefore, improving cell survival has been a primary objective of most therapeutic approaches. The subject invention provides for the use of melatonin or its derived analogs as a therapeutic approach in AD.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

| Ultrastructural Alterations of N2a Cells Induced by Aβ (25–35) | | |
|---|---|---|
| | Cell Blebbing (%) | Cell Retraction (%) |
| Scrambled Peptide | 11 ± 3 | 16.5 ± 2.5 |
| Aβ (25–35) | 93 ± 3 | 47.5 ± 8.5 |
| Aβ + Melatonin | 42 ± 3 | 27.5 ± 2.5 |

LIST OF REFERENCES CITED

Anderson, J. P., et al., Neurosci Lett 128:126–129 (1991).
Behl, C., et al., Biochem Biophys Res Commun 186:944–950 (1992).
Behl, C., et al., Brain Res 645:253–264 (1994).
Behl, C., et al., Cell 77:817–827 (1994).
Benitez-King, G., and Anton-Tay, F., Experientia 49(8) :635–641 (1993).

Burdick, D., et al., J Biol Chem 267:546–554 (1992).
Busciglio, J., et al., Neurobiol Aging 13:609–612 (1992).
Busciglio, J., et al., J Neurochem 61(4):1565–1568 (1993)
Butterfield, D. A., et al., Biochem Biophys Res Commun 200:710–715 (1994).
Capecchi, M., Cell 22:479–488 (1980).
Chartier-Harlin, M. C., et al., Nature 353(6347):844–846 (1991).
Copani, A., et al., Molecular Pharmacology 47(5):890–897 (1995).
Dori, D., et al., Chronobiol 21:121–126 (1994).
Furuta, A., et al., Am J Pathol 146:357–367 (1995).
Glenner, G. G., and Wong, C. W., Biochem Biophys Res Commun 120:885–890 (1984).
Goodman, Y., and Mattson, M. P., Exp Neurol 128:1–12 (1994).
Gschwind, M., and Huber, G., J Neurochem 65:292–300 (1995).
Haass, C., et al., Nature 359:322–324 (1992).
Harris, M. E., et al., Experimental Neurol 131:193–202 (1995).
Hayat, M. A., *Basic techniques for transmission electron microscopy.* Harcourt, Brace and Jovanovich, Academic Press (1986).
Hensley, K., et al., Proc Natl Acad Sci USA 91(8):3270–3274 (1994).
Huerto-Delgadillo, L., et al., J Pineal Res 17:55–62 (1994).
Hyman, B. T., et al., In: *Research advances in Alzheimers disease and related disorders.* Ed Iqbal, K., et al., John Wiley and Sons, pp. 453–560 (1985).
Iguchi, H., et al., J Clin Endocrinol Metabol 55:27–29 (1982).
Kennedy, A. M., et al., Brain 116:309–324 (1993).
Klein, T. M., et al., Nature 327:70–73 (1987).
Koopman, G., et al., Blood 84(5):1415–1420 (1994).
Le, W-D., et al., Brain Res 686:49–60 (1995).
Mannino, R. J., and Gould-Fogerite, S., BioTechniques 6:682–690 (1988).
Marin, M. C., et al., Oncogene 12:2259–2266 (1996).
Mark, R. J., et al., J Neurosci 15:6239–6249 (1995).
Mattson, M. P., Ann N Y Acad Sci 747:50–76 (1994).
Mattson, M. P., et al., Trends Neurosci 16:409–414 (1993).
Mattson, M. P., et al., J Neurosci 12:376–389 (1992).
Menendez-Pelaez, A., et al., J Cell Biochem 53:373–382 (1993).
Minta, A., et al., J Biol Chem 264(14):8171–8178 (1985).
Mishima, K., et al., Acta Psychiat Scand 89:1–7 (1994).
Nicotera, P., et al., Annu Rev Pharmacol Toxicol 32:449–470 (1992).
Omar, R. A., and Pappolla, M. A., Eur Ach Psychiatr Clin Neurosci 651:1–6 (1993).
Omar, R. A., et al., Cancer Res 47:3473–3476 (1987).
Pappolla, M. A., et al., Am J Pathol 140:621–628 (1992).
Pappolla, M. A., and Robakis, N. K., In: *Perspectives in behavioural medicine, Alzheimers disease and AIDS.* Eds Stein, M., and Baum, M., Academic Press, San Diego, Calif., pp. 3–20 (1995).
Pappolla, M. A., et al., Mol Chem Neuropathol 28:21–34 (1996).
Pierpaoli, W., Aging 3(2):99–101 (1991).
Pierpaoli, W., et al., Ann NY Acad Sci 621:291–313 (1991).
Pike, C. J., et al., J Neurosci 13:1676–1687 (1993).
Poot, M., et al., Cytometry 12:184–187 (1991).
Reiter, R. J., Exp Gerontol 30:199–212 (1995).
Robakis, N. K., and Pangalos, M. N., Neurobiol Aging 15:S127–129 (1994).
Robakis, N. K., et al., Proc Natl Acad Sci USA 84:4190–4194 (1987).
Rohn, T. T., et al., Chem Pharmacol 46:525–534 (1993).
Rothstein, J. D., et al., Proc Natl Acad Sci USA 91:4155–4159 (1994).
Sambamurti, K., et al., J Neurosci Res 33:319–329 (1992).
Sambrook, J., et al., *Molecular Cloning: A Laboratory Manual,* 2nd Ed., Cold Spring Harbor Laboratory, Cold Spring Harbor, NY (1989).
Shigekawa, K., and Dower, W. J., BioTechniques 6:742–751 (1988).
Shoji, M., et al., Science 258:126–129 (1992).
Skene, D. J., et al., Brain Research 528:170–174 (1990).
Smith, M. A., et al., Amer J Pathol 145:42–47 (1994).
Souetre, E., et al., Am J Psychiatry 146:1037–1040 (1989).
Vermes, I., et al., J Immunol Methods 184(1):39–51 (1995).
Vito, P., et al., Science 721:521–525 (1996).
Weidemann, A., et al., Cell 57:115–126 (1989).
Weiss, J. H., et al., J Neurochem 62(1):372–375 (1994).
Yankner, D. A., et al., Science 250:279–282 (1990).
Zhang, Z., et al., Neurosci Lett 177:162–164 (1994).
Zhao, X., et al., Comp Biochem Physiol 106:165–170 (1993).

What is claimed is:

1. A method of enhancing the survivability of cells that have been subjected to cytotoxic effects of amyloid beta protein comprising exposing said cells to an effective amount of melatonin.

2. The method of claim 1 wherein the exposure to melatonin results in a decrease in incidence of cell death.

3. The method of claim 1 where said cytotoxic effect is increased lipid peroxidation.

4. The method of claim 1 where said cytotoxic effect is increased intracellular $Ca^{2+}$.

5. The method of claim 1 wherein said cytotoxic effect is increased oxygen-centered free radicals.

6. The method of claim 1 wherein said cells are neuronal cells.

7. The method of claim 1 wherein said cells are present in a human subject and said exposing results from systemic administration of said melatonin.

8. The method of claim 7 wherein said effective amount is between about 1 $\mu$g and about 100 g melatonin.

9. The method of claim 1 wherein said cells are present in a human subject having Alzheimer's disease.

10. The method of claim 1 wherein said effective amount is between about 1 and 100 $\mu$M melatonin.

11. A method of enhancing the survivability of cells that have been subjected to cytotoxic effects of amyloid beta protein in a patient afflicted with Alzheimer's disease, comprising administering melatonin to the patient in an amount effective to alleviate symptoms associated with said disease.

12. The method of claim 11 wherein the amount is between about 1 $\mu$g and about 100 g melatonin.

13. The method of claim 11 wherein said administering is systemic.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 11 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

Lys Ser Gly Asn Met Leu Gly Ile Ile Ala Gly
   1             5                10